United States Patent [19]

Young, Jr. et al.

[11] Patent Number: 4,948,910
[45] Date of Patent: Aug. 14, 1990

[54] OXYDEHYDROGENATION OF SATURATED ALIPHATIC NITRILES OVER A CARBON CATALYST

[76] Inventors: Harold W. Young, Jr., 1807 Dilloway; Gerald L. Curnutt, 2800 Mt. Vernon, both of Midland, Mich. 48640

[21] Appl. No.: 206,260

[22] Filed: Jun. 13, 1988

[51] Int. Cl.$^5$ ................. C07C 121/30; C07C 121/48; C07C 121/70
[52] U.S. Cl. .................................................... 558/383
[58] Field of Search .......................................... 558/383

[56] References Cited

U.S. PATENT DOCUMENTS

| | | | |
|---|---|---|---|
| 2,399,349 | 4/1946 | Hochwolt | 260/464 |
| 2,434,606 | 1/1948 | Carpenter | 260/464 |
| 2,438,019 | 3/1948 | Pace | 260/464 |
| 2,471,767 | 5/1949 | Mowry et al. | 260/465.8 |
| 3,313,840 | 4/1967 | Kosel et al. | 260/465.8 |
| 3,497,564 | 2/1970 | Allen et al. | 260/650 |
| 3,855,268 | 12/1974 | Duke, Jr. | 260/465.3 |
| 3,959,345 | 5/1976 | Morita et al. | 260/465.8 R |
| 3,965,141 | 6/1976 | Leimgruber et al. | 260/465.5 R |
| 4,040,990 | 8/1977 | Neely | 260/2.1 R |
| 4,436,671 | 3/1984 | Furuoya et al. | 260/465.3 |

FOREIGN PATENT DOCUMENTS

| | | | |
|---|---|---|---|
| 745181 | 10/1966 | Canada | 558/383 |
| 42-17965 | 9/1967 | Japan . | |
| 353538 | 12/1977 | U.S.S.R. . | |
| 739050 | 8/1980 | U.S.S.R. . | |
| 781197 | 11/1980 | U.S.S.R. . | |

OTHER PUBLICATIONS

Derwent 61332 W/37 (ca: 1975).
N. Tsubokawa et al., Bulletin of the Chemical Society of Japan, 55, 3541-3545 (1982).
K. Fujimoto et al., Journal Japan Petroleum Institute, 25, (1), 20, 1982.
A. E. Lisovskii et al., Kinetika i Kataliz, 19, 760-763 (1979), [Translated from Russian Kinet. i Kat., 19, 950-954, (1978)].
T. G. Alkhazov et al., Kinetika i Kataliz, 19, 482-485 (1978), [Translated from Kinet. i Kat., 19,611-614 (1978)].
T. G. Alkhazov et al., Reaction Kinetics and Catalysis Letters, 12, 189-193 (1979).
Noller, "Chemistry of Organic Compounds", 3rd ed., 1966, pp. 275-276.
Hawley, "The Condensed Chemical Dictionary", 10th ed., 1981, pp. 30, 730, 910, 1070.

*Primary Examiner*—Joseph Paul Brust

[57] ABSTRACT

A process for preparing an unsaturated aliphatic nitrile comprising contacting a saturated aliphatic nitrile with oxygen in the presence of a carbon catalyst under conditions such that the unsaturated aliphatic nitrile is formed. A preferred form of the catalyst is a carbon prepared by the pyrolysis of a synthetic polymer. Unsaturated aliphatic nitriles, such as acrylonitrile, fumaronitrile and maleonitrile, are prepared in high selectivity by this process.

1 Claim, No Drawings

OXYDEHYDROGENATION OF SATURATED ALIPHATIC NITRILES OVER A CARBON CATALYST

BACKGROUND OF THE INVENTION

This invention pertains to an oxydehydrogenation process for preparing unsaturated aliphatic nitriles, such as acrylonitrile, fumaronitrile and maleonitrile.

Unsaturated aliphatic nitriles are useful comonomers in the formation of polymers having high heat and solvent resistance.

Certain catalysts are known for the oxydehydrogenation of saturated aliphatic nitriles to unsaturated aliphatic nitriles. U.S. Pat. No. 3,855,268 teaches the oxydehydrogenation of an alkylnitrile comprising forming a reaction mixture comprising the nitrile, an iodine-containing promoter, and oxygen, and passing the reaction mixture over a substantially inert material, such as carborundum, and then over a metal chromite catalyst. This process uses iodine, which must be separated from the products.

U.S. Pat. No. 3,965,141 teaches a process for the preparation of dialkyl aminoacrylonitrile by treating dimethylaminopropionitrile with a hydrogen acceptor in the presence of a dehydrogenation catalyst, such as Raney nickel, palladium or copper chromite. This process requires long reaction times and employs expensive hydrogen acceptors such as vinyl ethers and cyclic ethers.

U.S. Pat. No. 3,313,840 describes the catalytic oxydehydrogenation of succinic acid dinitrile to fumaronitrile and maleonitrile in the presence of at least one oxide of an element of Groups Vb and VIb of the Periodic Table. The preferred oxides are vanadium pentoxide, molybdenum trioxide, and particularly chromium (III) oxide. The dinitriles are produced in a constant ratio of fumaronitrile to maleonitrile of 5:4.

The above-identified processes are typically restricted to preparing narrow classes of nitrile products. Moreover, the known processes are costly, because they employ expensive metal catalysts, hydrogen acceptors, or promoters. Even more disadvantageously, the known processes are slow and inefficient. Accordingly, the known processes are not available for industrial adaptation.

It would be desirable to have a direct catalytic process for preparing an unsaturated aliphatic nitrile from a saturated aliphatic nitrile. It would be more desirable if such a process was capable of producing a wide range of unsaturated aliphatic nitrile products. It would be even more desirable if such a process produced essentially no by-products or waste stream. Finally, it would be highly advantageous if such a process was efficient, inexpensive and otherwise adaptable for industrial use.

SUMMARY OF THE INVENTION

This invention is a process for preparing an unsaturated aliphatic nitrile comprising contacting a saturated aliphatic nitrile with oxygen in the presence of a catalyst under conditions such that the unsaturated aliphatic nitrile is formed. The catalyst contains carbon which is essentially free of platinum group metals. The phrase "essentially free" means that the catalyst contains less than about 0.1 weight percent of each metal.

The aforementioned process of this invention is direct and catalytic. Advantageously, the process can be used to prepare a wide variety of unsaturated aliphatic nitriles, including acrylonitrile, crotononitrile, fumaronitrile, maleonitrile, and 1,2-disubstituted-1,2-ethylene dinitriles. Even more advantageously, the process of this invention produces relatively few by-products. The major by-product of the process is water. Most advantageously, the process of this invention is adaptable for industrial use. Furthermore, as applied to the oxydehydrogenation of succinonitrile, the process of this invention can produce significantly more fumaronitrile than maleonitrile.

The unsaturated aliphatic nitriles, which are produced by the process of this invention, are useful as starting comonomers in the synthesis of polymers, for example, in copolymerizations with styrene. The polymers which are produced from these unsaturated nitriles show high heat and solvent resistance. In addition, the unsaturated aliphatic nitriles, which are produced by the process of this invention, are useful as starting materials for pharmaceuticals, such as pyridoxine (vitamin $B_6$), and useful as cyanoalkylation reagents and in Diels-Alder reactions.

DETAILED DESCRIPTION OF THE INVENTION

The saturated aliphatic nitriles which can be oxydehydrogenated by the process of this invention include any saturated aliphatic compound containing at least two adjacent carbon atoms each of which is bound to at least one hydrogen atom, and also containing at least one carbon atom which is bound to a nitrile moiety ($-C\equiv N$). Preferably, the nitrile moiety is bound to one of the above-identified adjacent carbon atoms. Such compounds include, but are not limited to, saturated aliphatic mononitriles, such as propionitrile, butyronitrile, cyclobutanecarbonitrile, 2-methylbutyronitrile, valeronitrile, cyclopentanecarbonitrile, capronitrile, cyclohexanecarbonitrile, enanthonitrile, cycloheptanecarbonitrile, caprylonitrile, pelargonitrile, 3-methylcycloheptanecarbonitrile, cyclooctanecarbonitrile, undecanenitrile, lauronitrile, tridecanenitrile, myristonitrile, and stearonitrile: as well as saturated aliphatic dinitriles and polynitriles, such as succinonitrile, glutaronitrile, adiponitrile, 1,3,5-tricyanopentane, 1,2-cyclobutanedicarbonitrile, 1,4-cyclohexanedicarbonitrile, and the like.

The preferred saturated aliphatic nitriles can be represented by the general formula:

$$N\equiv C-CHR^1-CHR^2-(CR^3_2)_m-R^4 \tag{1}$$

wherein m is a positive integer from 0 to about 10; $R^1$, $R^2$, and $R^3$ are each independently hydrogen or an inert $C_1-C_{20}$ organic moiety: and $R^4$ is hydrogen, nitrile ($-C\equiv N$), or an inert $C_1-C_{20}$ organic moiety. For the purposes of this invention, an "inert organic moiety" is an unsubstituted or substituted hydrocarbyl moiety that is non-reactive and does not hinder the oxydehydrogenation process of this invention. Hydrocarbyl moieties are comprised of atoms of carbon and hydrogen. A substituted hydrocarbyl moiety is one containing atoms other than carbon and hydrogen, such as oxygen in ether and carbonyl moieties, or halogens like chlorine or bromine. The substituted hydrocarbyl moieties are acceptable providing they are inert, as defined hereinabove. Preferably, $R^1$, $R^2$, and $R^3$ are each independently hydrogen: or an alkyl, aryl, aralkyl, or alkaryl hydrocarbyl moiety having from 1 to about 12 carbon atoms. More preferably, $R^1$, $R^2$, and $R^3$ are each independently hydrogen, methyl or ethyl. Most preferably, $R^1$, $R^2$, and $R^3$ are each independently hydrogen. Preferably, $R^4$ is hydrogen; nitrile (—C≡N); or an alkyl, aryl, aralkyl, or alkaryl hydrocarbyl moiety having from 1 to about 12 carbon atoms. More preferably, $R^4$ is nitrile (—C≡N). Preferably, m is zero. In the most preferred case, m is zero and $R^4$ is nitrile (—C≡N). Thus, the most preferred saturated aliphatic dinitriles are 1,2-ethane dinitriles, sometimes referred to hereinafter as "succinonitriles," which can be represented by the general formula:

$$N\equiv C-CHR^1-CHR^2-C\equiv N \quad (II)$$

wherein $R^1$ and $R^2$ are defined hereinbefore. Among these succinonitriles, it is preferred that $R^1$ and $R^2$ be hydrogen, such that the preferred compound is succinonitrile.

The saturated aliphatic nitriles, identified hereinbefore, are commercially available or can be prepared by known methods. One preferred method of preparing 1,2-ethane dinitriles is described in U.S. Pat. No. 2,434,606, incorporated herein by reference. For example, the preferred method of obtaining the compound succinonitrile involves the reaction of acrylonitrile with hydrocyanic acid in the presence of a base, such as an alkali metal hydroxide or tertiary amine.

In addition to the saturated aliphatic nitrile, oxygen is employed in the process of this invention. The oxygen is typically supplied from a gaseous source provided as a continuous oxygen-containing feed. Any source of oxygen is acceptable, such as pure gaseous elemental oxygen, air, ozone, or nitrous oxide. The preferred source of oxygen is elemental oxygen. More preferably, the gaseous elemental oxygen is diluted with a non-reactive gas such as nitrogen, helium, argon, or water vapor, in order to control the exotherm from the reaction. Preferably, the diluent is nitrogen. The oxygen content of the mixture comprising oxygen and the non-reactive gas is preferably not greater than about 30 mole percent. More preferably, the oxygen content of the mixture ranges from about 1 mole percent to about 22 mole percent. Most preferably, the oxygen content of the mixture ranges from about 1 mole percent to about 7 mole percent.

The amount of oxygen relative to the amount of saturated aliphatic nitrile can be any ratio which is sufficient to promote the oxydehydrogenation process of this invention. Preferably, the molar ratio of oxygen to saturated aliphatic nitrile is in the range from about 0.01:1 to about 10:1. More preferably, the molar ratio of oxygen to saturated aliphatic nitrile is in the range from about 0.1:1 to about 5:1; most preferably, from about 0.5:1 to about 3:1. Below the preferred lower limit there may not be sufficient oxygen present to carry out the oxydehydrogenation reaction, and the conversion of the saturated aliphatic nitrile may be low. Above the preferred upper limit the selectivity for deep oxidation products, such as carbon dioxide, increases. Moreover, above the preferred upper limit the mole ratio may fall within the explosive range for mixtures of the nitrile and oxygen. It is recommended to operate the process outside the explosive limits in order to minimize the risk of a runaway reaction.

The catalyst employed in the process of this invention comprises carbon which is essentially free of platinum group metals; namely, ruthenium, rhodium, palladium, osmium, iridium, and platinum. Preferably, the catalyst is essentially free of transition metals, including the platinum group metals, and the lanthanide rare earth metals (atomic numbers 57-71). The transition metals include the metals of Groups IB, IIB, IIIB, IVB, VB, VIB, VIIB, and VIII of the Periodic Table. The term "essentially free" means that the carbon contains less than about 0.1 weight percent of each of the aforementioned metals. Preferably, the carbon contains less than about 0.05 weight percent of each metal: more preferably, less than about 100 ppm of each metal. Although metals are not required to be present in the catalyst, optionally, metals may be present and may act as promoters of the catalyst. For example, the transition metals and rare earth metals may be present at the low concentrations specified hereinbefore. Metals other than the above-identified metals, such as metals of Groups IA and IIA, may be present at higher concentrations, that is higher than 0.1 weight percent.

Any form of carbon which catalyzes the oxidative dehydrogenation of the saturated aliphatic nitrile to an unsaturated aliphatic nitrile product is acceptable. Thus, carbon derived from any animal, plant or mineral source can be used. Examples of suitable carbon catalysts include, but are not limited to the following: activated carbons such as those derived from coal, wood or animal bones: carbon blacks such as those derived from gas phase pyrolysis of hydrocarbons; natural or synthetic graphites or graphite whiskers; supported pyrolytic carbons wherein the support is an inorganic refractory oxide, inorganic phosphate, inorganic boride, or inorganic nitride; cokes such as those obtained from the destructive distillation of bituminous coal, petroleum, and coal-tar pitch; and chars and polymeric carbons prepared by pyrolysis of resinous polymers. Additionally, it is acceptable to employ high surface area carbons prepared by direct chemical activation. Such chemically activated, high surface area carbons are described by T. M. O'Grady and A. N. Wennerberg in *Petroleum-Derived Carbons*, American Chemical Society Symposium Series, Vol. 303, J. D. Bacha et al., eds., American Chemical Society Publications, Washington, D.C., 1986. The preparation of these high surface area carbons involves reacting petroleum coke or other carbonaceous sources with excess potassium hydroxide at about 450° C. to obtain an intermediate product which is subsequently pyrolyzed at about 850° C. to the high surface area carbon.

Some of the above-identified carbons, for example the activated carbons and graphites, are "soft" carbons which are known to break apart easily and slough dust particles. Others of the above-identified carbons are non-graphitizable or "hard" carbons, which are known to possess good structural integrity and do not slough dust particles. The carbons prepared by the pyrolysis of resinous polymers are an example of hard carbons. Preferably, the catalyst employed in the process of this invention is a hard carbon. More preferably, the catalyst employed in the process of this invention is a hard carbon prepared by the pyrolysis of a resinous polymer.

The hard carbon catalysts which are prepared by the pyrolysis of resinous polymers are known in the art. The catalysts and their method of preparation are described in U.S. Pat. No. 4,040,990, which is incorporated herein by reference. As described therein, these carbons are partially pyrolyzed particles preferably in the form of hard beads or spheres. They are produced by the controlled decomposition of a synthetic polymer.

The pyrolysis, as described in U.S. Pat. No. 4,040,990, is generally conducted in an inert atmosphere comprised of, for example, helium, argon, or nitrogen. Preferably, the polymer is heated rapidly to a maximum temperature in the range from about 300° C. to about 900° C.; heated at the maximum temperature for a period of up to about 20 minutes; and cooled to room temperature before exposing to air. For the purposes of this invention, maximum temperatures of up to about 1200° C. are also suitable, and longer heating times are not deleterious.

Any of the many synthetic polymers, disclosed in U.S. Pat. No. 4,040,990 and incorporated herein by reference, can be employed in preparing the hard carbon catalyst for the process of this invention. Preferred are polymers derived from aliphatic and aromatic materials which are ethylenically unsaturated. Preferably, the polymer is cross-linked, because cross-linking stabilizes the polymer thermally and leads to greater carbon yields. Preferably also, the polymer contains a carbon-fixing moiety, such as a cation, anion, strong base, weak base, sulfonic acid, carboxylic acid, halogen, or alkylamine moiety. The more preferred polymers include polyvinylidene chloride, and macroreticular ion-exchange resins derived from aliphatic and aromatic materials which are ethylenically unsaturated. Most preferably, the polymer is a polystyrene divinylbenzene sulfonic acid ion-exchange resin.

The preferred hard carbon catalyst, which is prepared by the pyrolysis of a resinous polymer, contains at least three distinct sets of pores of differing average size. One set comprises large pores, mesopores, which originate from the resinous starting material, and typically range in size from about 35 Å to about 300 Å in average critical dimension. The second set comprises intermediate pores, micropores, which typically range in size from about 7 Å to about 35 Å. The third set and smallest pores, sub-micropores, originate on pyrolysis of the resinous polymer. These small pores are typically less than about 7 Å in average critical dimension; however, the exact size depends on the temperature of pyrolysis. In addition to pore size, the pyrolysis temperature also controls total pore volumes. Generally, as the pyrolysis temperature increases, the mesopore volume decreases and the sub-micropore volume increases. However, at pyrolysis temperatures above 900° C. the sub-micropore volume is low. It is believed that the sub-micropores control the product selectivities in the oxydehydrogenation reaction; however, such a theory should not be construed to be binding or limiting of the scope of the invention. Preferably, the sub-micropore volume of the pyrolyzed carbon catalyst of this invention is at least about 0.01 ml/g. More preferably, the sub-micropore volume of the pyrolyzed carbon catalyst of this invention is at least about 0.10 ml/g. Most preferably, the sub-micropore volume of the pyrolyzed carbon catalyst of this invention is at least about 0.15 ml/g. The measurement of porosity is derived from surface area and pore volume measurements obtained on any suitable instrument, such as a Micromeritics DIGISORB® 2500 unit, using nitrogen as the adsorbate at the boiling point of nitrogen, 77K. The methods used to obtain surface area and pore volumes are described by S. Lowell in *Introduction to Powder Surface Area* (John Wiley & Sons, 1979), or in the manuals provided with the DIGISORB® 2500 instrument made by the Micromeritics Instrument Corporation.

The carbon catalyst of this invention can possess any surface area providing the catalyst is active in the oxydehydrogenation reaction. Generally, the carbon catalyst possesses a surface area of at least about 10 $m^2/g$. Preferably, the carbon catalyst possesses a surface area of at least about 50 $m^2/g$; more preferably, a surface area in the range from about 100 $m^2/g$ to about 1500 $m^2/g$; most preferably, in the range from about 400 $m^2/g$ to about 700 $m^2/g$. The surface area is measured by the Brunauer-Emmett-Teller (BET) method. The BET method is described by R. B. Anderson, in *Experimental Methods in Catalytic Research*, Academic Press, 1968, pp. 48–66.

The saturated aliphatic nitrile can be delivered to the catalyst bed as a vapor phase feed or as a liquid phase feed. Preferably, the saturated aliphatic nitrile is fed into the catalyst bed as a vapor pre-mixed with the oxygen-containing gas. However, liquid phase feeds can be employed especially with higher molecular weight reactants and products.

Any suitable technique can be employed to obtain the preferred vapor phase feed comprising the reactant nitrile. Since the liquid phase usually has a higher vapor pressure than the solid phase, solid nitrile reactants can be melted to obtain the vapor phase feed. Alternatively, solid nitrile reactants can be sublimed to obtain the vapor phase feed. Preferably, however, the reactant nitrile is fed into the reactor at moderate or lower temperatures, taken as less than about 175° C. In order to operate at lower temperatures where the volatility of the liquid nitrile reactant is also lower, liquid solvents can be used to form a liquid phase feed. The liquid phase can be a solution or a heterogeneous mixture such as multiple immiscible liquid phases, suspensions or emulsions. Appropriate solvents include acetone, toluene, acetonitrile, water, and chlorinated hydrocarbons such as carbon tetrachloride. Preferably, the solvent is water; more preferably the solvent is water when the reactant nitrile is succinonitrile. Preferably, the minimum amount of solvent is employed, such that the reactant nitrile forms a nearly saturated solution with the solvent. For example, when the solvent is water and the reactant is succinonitrile, the preferred solution at about normal temperature and pressure, taken as 21° C. and 1 atmosphere, comprises about 8 weight percent water and 92 weight percent succinonitrile, which is near the eutectic ratio.

Any operable reaction temperature which allows the oxydehydrogenation reaction to proceed to the desired unsaturated aliphatic nitrile product is acceptable. Typically, the reaction is conducted at elevated temperatures. Preferably, the reaction temperature is controlled to minimize the reaction exotherm, described in more detail hereinafter. Preferably, the reaction temperature is in the range from about 300° C. to about 500° C.; more preferably, in the range from about 330° C. to about 450° C.; most preferably, in the range from about 350° C. to about 400° C. Below the preferred lower reaction temperature the conversion of the saturated aliphatic nitrile may be too low. Above the preferred upper reaction temperature the reaction may exotherm too much. Also, the selectivity to the desired unsaturated aliphatic nitrile products may decrease, as more deep oxidation products are formed.

Likewise, any operable reaction pressure is acceptable providing the oxydehydrogenation of the saturated aliphatic nitrile proceeds to the desired unsaturated aliphatic nitrile product. Preferably, the pressure of the oxydehydrogenation reaction is in the range from about 0.1 psia to about 1500 psia. More preferably, the pressure is in the range from about 1.5 psia to about 150 psia; most preferably, from about 7 psia to about 45 psia.

The reactor can have any style or design so long as the oxydehydrogenation process of this invention is allowed to proceed unhindered. An exotherm within the catalyst bed is typically present during the oxydehydrogenation reaction, and can be as high as 40° C. Reactor configurations, therefore, are preferably chosen to minimize the exotherm. For example, a tube-and-shell reactor can be employed with the catalyst packed in the tube and a heat-transferring means, such as steam, an organic heat-transfer fluid or molten salt bath, circulated on the shell side. Alternatively, a fluidized bed reactor can be employed. Other reactor configurations will be apparent to those skilled in the art. Preferred reactor designs, include the fixed-bed reactor or fluidized-bed reactor.

When operating the reaction in the liquid phase, any liquid hourly space velocity is suitable which provides the desired unsaturated aliphatic nitrile product. The preferred liquid hourly space velocity can vary depending on the specific form of the catalyst, the specific saturated nitrile reactant, the amount of oxygen, and the reaction temperature and pressure. The liquid hourly space velocity is expressed in units of cc solution of liquefied saturated aliphatic nitrile per hour per cc catalyst, or simply $hr^{-1}$. Preferably, the liquid hourly space velocity ranges from about 0.001 $hr^{-1}$ to about 50 $hr^{-1}$; more preferably, from about 0.01 $hr^{-1}$ to about 10 $hr^{-1}$; most preferably, from about 0.1 $hr^{-1}$ to about 5 $hr^{-1}$.

The oxydehydrogenation reaction results in the loss of at least two hydrogen atoms from the saturated aliphatic nitrile reactant. The products which are produced are unsaturated aliphatic nitriles. For example, propionitrile loses two hydrogen atoms to yield acrylonitrile; and succinonitrile loses two hydrogen atoms to yield the trans and cis unsaturated isomers, fumaronitrile and maleonitrile, respectively. The preferred unsaturated aliphatic nitriles can be represented by the general formula:

$$N \equiv C - CR^1 = CR^2 - (CR^3_2)_m - R^4 \quad (III)$$

wherein m is a positive integer from 0 to about 10; $R^1$, $R^2$, and $R^3$ are each independently hydrogen or an inert $C_1$–$C_{20}$ organic moiety; and $R^4$ is hydrogen, nitrile (—C≡N), or an inert $C_1$–$C_{20}$ organic moiety, as defined hereinbefore. Preferably, $R^1$, $R^2$, and $R^3$ are each independently hydrogen; or an alkyl, aryl, aralkyl, or alkaryl hydrocarbyl moiety having from 1 to about 12 carbon atoms. More preferably, $R^1$, $R^2$, and $R^3$ are each independently hydrogen, methyl or ethyl; most preferably, hydrogen. Preferably, $R^4$ is hydrogen; nitrile; or an alkyl, aryl, aralkyl, or alkaryl hydrocarbyl moiety having from 1 to about 12 carbon atoms. More preferably, $R^4$ is nitrile. Isomers of compounds of Formula III can also be formed, wherein the unsaturation occurs at any other location along the carbon chain. Preferably, the unsaturation occurs at a carbon atom directly bonded to a nitrile moiety, as shown in Formula III. Such products may be thermodynamically favored due to conjugation of the double bond with the nitrile moiety. Even more unsaturated variants of Formula III can be formed, wherein further oxydehydrogenation has occurred to yield more than one ethylenic double bond.

Most preferably, $R^4$ in Formula III is nitrile, and m is 0, such that the unsaturated aliphatic nitrile product is a trans-1,2-ethylene dinitrile represented by the general formula:

or a cis-1,2-ethylene dinitrile represented by the general formula:

$R^1$ and $R^2$ in Formulas IV and V are defined hereinbefore. Most preferably, $R^1$ and $R^2$ are hydrogen, and the products are fumaronitrile and maleonitrile obtained in the oxydehydrogenation of succinonitrile.

For the purposes of this invention, "Conversion" is defined as the mole percentage of saturated aliphatic nitrile which is lost from the reactant stream as a result of reaction. Typically, the conversion varies depending upon the reactants, process conditions, and type of carbon catalyst employed. Within the preferred temperature range, as the temperature increases the conversion generally increases. Within the preferred space velocity range, as the space velocity increases the conversion usually decreases. Preferably, the conversion of the saturated aliphatic nitrile is at least about 5 mole percent; more preferably, at least about 10 mole percent; most preferably, at least about 15 mole percent.

In a flow-type reactor the effluent product stream may contain unreacted saturated aliphatic nitrile. It is possible to remove the unsaturated products from the effluent stream, and recycle the unreacted saturated aliphatic nitrile back to the reactor. The recycle ratio is the ratio of moles of unreacted saturated aliphatic nitrile in the effluent which are returned to the feed to moles of fresh saturated aliphatic nitrile in the feed. Recycle ratios can vary from zero to any number which results in the formation of product. Preferably, unreacted feed is recycled at a recycle ratio from about 0.1 to about 10.

For the purposes of this invention "Selectivity" is defined as the mole percentage of converted saturated aliphatic nitrile which forms unsaturated aliphatic nitrile products. The selectivity varies depending upon the reactants, the process conditions, and the form of the carbon catalyst employed. Within the preferred temperature range, as the temperature increases the selectivity to unsaturated aliphatic nitriles usually decreases. Within the preferred space velocity range, as the space velocity increases the selectivity to unsaturated aliphatic nitriles usually increases. Additionally, the selectivity to unsaturated aliphatic nitriles often increases as the oxygen concentration decreases. Typically, 1,2-ethane dinitriles are oxydehydrogenated to cis- and trans-1,2-ethylene dinitriles in a combined selectivity of at least about 50 mole percent; preferably, at least about 60 mole percent; more preferably, at least about 65 mole percent. Typically, the process of this invention produces significantly more trans-1,2-ethylene dinitriles than cis-1,2-ethylene dinitriles. Preferably, the mole ratio of trans-1,2-ethylene dinitriles to cis-1,2-ethylene dinitriles is at least about 1.0; more preferably, at least about 1.5; most preferably, at least about 2.0.

The unsaturated aliphatic nitrile products are recovered by methods well-known in the art. In liquid phase reactions the products are readily collected in containers, and any solvents are distilled out. In gas phase reactions the product is preferably trapped in an air- or water-cooled condenser, and collected as a liquid or solid. Purification of the products can be accomplished by known methods. A preferred method is that of Kosel et al, as described in U.S. Pat. No. 3,313,840 incorporated herein by reference. Typically, the products are hygroscopic, and thus, they may contain water. If desired, the water can be removed by known means such as distillation or use of drying agents, such as silica and molecular sieves.

By-products vary depending upon the reactants. For example, when the reactant nitrile is the compound succinonitrile, trace amounts of acrylonitrile and acetonitrile are formed. In addition, by-products such as ammonia and carbon oxides may be produced by "deep oxidation" of the saturated aliphatic nitriles. These, too, can be removed, if desired, by known methods such as distillation, chromatography, use of adsorbents such as activated carbon and molecular sieves, or recrystallization, as applicable.

ILLUSTRATIVE EMBODIMENTS

The following examples further illustrate the invention. In the examples, the reactants and solvents are of reagent grade or higher quality. Percentages are in mole percent units, unless otherwise noted.

EXAMPLE 1

Preparation of the Carbon Catalyst

An ion-exchange resin in the acid form comprising sulfonated polystyrene containing 20 weight percent divinylbenzene (DOWEX ® MSC-1, The Dow Chemical Company) is air dried below 150° C. to less than 20 weight percent residual moisture. The dried resin analyzes as 50.90 percent carbon, 4.94 percent hydrogen, and 17.0 percent sulfur. The air-dried resin is carbonized in a quartz reactor by heating under a flow of oxygen-free nitrogen while increasing the temperature from ambient to 600° C. at a rate of 100° C./hr. The rate of nitrogen flow is 200 cc/min. After the temperature reaches 600° C., the carbonization is continued for one additional hour. After the carbonization is complete, the carbon is cooled to ambient temperature under a nitrogen flow, at which time the carbon is exposed to air. The carbon appears in the form of small, hard spheres having a surface area of 635 m$^2$/g, as determined by the BET method for N$_2$ adsorption. The carbon analyzes as 88±3 percent carbon, 2.9±0.2 percent hydrogen, and 5.2±0.1 percent sulfur. Elemental analysis by X-ray fluorescence shows traces of calcium, aluminum, iron, chromium, copper, and nickel, each at a concentration less than 100 ppm. Magnesium is present at a concentration of 225 ppm. No traces of platinum group metals are found. The porosity, as determined by a t-plot analysis, comprises 0.18 ml/g sub-micropores, 0.03 ml/g micropores, and 0.39 ml/g mesopores.

EXAMPLE 2

Oxydehydrogenation of Succinonitrile

The carbon catalyst (10 ml) prepared in Example 1 is loaded into a stainless steel tube reactor (10 inches × ½-inch dia.). The catalyst bed is supported on silicon carbide (10 ml), and silicon carbide (10 ml) is also placed on top of the catalyst bed. A gaseous mixture of nitrogen and oxygen in a N$_2$/O$_2$ mole ratio of 96/4 is passed through the catalyst bed at a gas hourly space velocity of 1075 hr$^{-1}$. The temperature of the reactor is raised to and maintained at the maximum temperature indicated in Table I. An aqueous solution of succinonitrile (87 weight percent) is passed through the catalyst bed at a liquid hourly space velocity of 0.5 hr$^{-1}$. The products are collected in a cold trap and are periodically analyzed by gas chromatography on a DB-210 capillary column (30 m × 0.25 mm dia.) with the results shown in Table I.

TABLE I

| Temp (°C.) | SN Conversion (mole %) | FN + MN Selectivity (mole %) | FN/MN Mole Ratio |
|---|---|---|---|
| 300 | 1.9 | 71.7 | 1.3 |
| 350 | 7.0 | 86.6 | 1.7 |
| 380 | 13.9 | 73.7 | 2.6 |
| 400 | 14.9 | 87.1 | 2.1 |
| 410 | 19.5 | 57.1 | 1.9 |

SN = succinonitrile;
FN = fumaronitrile;
MN = maleonitrile

The data show that the conversion of succinonitrile increases as the reaction temperature increases. Moreover, at reaction temperatures less than 400° C. the combined selectivity to fumaronitrile and maleonitrile varies between about 72 percent and about 87 percent. Above 400° C. the combined selectivity to fumaronitrile and maleonitrile decreases. The fumaronitrile to maleonitrile mole ratio ranges from 1.3 to 2.6 over the temperature range from 300° C. to 380° C.

EXAMPLE 3

Oxydehydrogenation of Propionitrile

The catalyst of Example 1 is used in the reactor of Example 2 to oxydehydrogenate propionitrile. The general procedure of Example 2 is followed with the exception that the feed is pure propionitrile and no water is added. The results are given in Table II.

TABLE II

| Temp (°C.) | PN Conversion (mole %) | AN Selectivity (mole %) |
|---|---|---|
| 400 | 3.7 | 40.2 |
| 430 | 5.6 | 66.1 |
| 450 | 4.5 | 82.0 |
| 470 | 5.9 | 64.2 |

PN = propionitrile;
AN = acrylonitrile

The data show that the conversion of propionitrile tends to increase as the temperature increases. Moreover, the selectivity to acrylonitrile reaches a maximum of 82.0 percent at a reaction temperature of 450° C.

EXAMPLE 4

Oxydehydrogenation of Butyronitrile

The catalyst of Example 1 is used in the reactor of Example 2 to oxydehydrogenate butyronitrile. The general procedure of Example 2 is followed with the exception that the feed is pure butyronitrile and no water is added. The results, shown in the sequence in which the experiments are conducted, are given in Table III.

TABLE III

| Temp (°C.) | BN Conversion (mole %) | CN Selectivity (mole %) | Trans/Cis Mole Ratio |
| --- | --- | --- | --- |
| 400 | 4.6 | 34.7 | 1.6 |
| 450 | 6.3 | 45.2 | 1.5 |
| 470 | 6.6 | 49.9 | 1.4 |
| 420 | 5.0 | 34.7 | 1.5 |
| 400 | 4.0 | 40.3 | 1.6 |

BN = butyronitrile;
CN = crotononitrile

The data show that the conversion of butyronitrile and the selectivity to crotononitrile generally increase with an increase in reaction temperature. Moreover, the trans/cis mole ratio of crotononitrile isomers is relatively constant over the temperature range tested. It is further noted that the catalyst is essentially unchanged on cycling from a temperature of 400° C. to 470° C. and back to 400° C. Allyl cyanide is present as a by-product in small amounts.

EXAMPLE 5

Preparation of Carbon Catalyst

The general procedure of Example 1 is employed to prepare a carbon catalyst with the exception that the resinous polymer is polyvinylidene chloride (SARANT® PVDC, The Dow Chemical Company). No traces of platinum group metals are found in the pyrolyzed carbon at levels as low as 10 ppm. No other metals are found in the pyrolyzed carbon at concentrations higher than 100 ppm.

EXAMPLE 6

Oxydehydrogenation of Succinonitrile

The carbon catalyst of Example 5 is employed in the oxydehydrogenation of succinonitrile. The general procedure of Example 2 is followed with the results shown in Table IV.

TABLE IV

| Temp (°C.) | SN Conversion (mole %) | FN + MN Selectivity (mole %) | FN/MN Mole Ratio |
| --- | --- | --- | --- |
| 400 | 35.3 | 30.4 | 1.2 |
| 350 | 14.8 | 53.0 | 0.8 |
| 300 | 2.6 | 82.4 | 0.8 |
| 330 | 6.1 | 87.4 | 0.8 |
| 370 | 19.6 | 48.2 | 0.8 |

SN = succinonitrile;
FN = fumaronitrile;
MN = maleonitrile

The data show that the conversion of succinonitrile increases with an increase in reaction temperature, while the combined selectivity to fumaronitrile and maleonitrile is greatest at the lower reaction temperatures. The fumaronitrile to maleonitrile mole ratio is close to about 1.0 at all of the reaction temperatures tested. It is further noted that the catalyst is essentially unchanged upon recycling from a temperature of 400° C. to 300° C. and back to 370° C.

What is claimed is:

1. A process for preparing an unsaturated aliphatic nitrile having the formula:

wherein m is a positive integer from 0 to about 10; $R^1$, $R^2$, and $R^3$ are each independently hydrogen or an alkyl, aryl, aralkyl, or alkaryl hydrocarbyl moiety having from 1 to about 12 carbon atoms; and $R^4$ is hydrogen, nitrile (—C≡N), or an alkyl, aryl, aralkyl, or alkaryl hydrocarbyl moiety having from 1 to about 12 carbon atoms, the process comprising contacting a saturated aliphatic nitrile having the formula:

wherein m, $R^1$, $R^2$, $R^3$, and $R^4$ are defined hereinabove, with gaseous oxygen in the presence of a carbon catalyst at a temperature in the range from about 330° C. to about 450° C., a pressure in the range from about 1.5 psia to about 150 psia, and a space velocity in the range from about 0.01 hr$^{-1}$ to about 10 hr$^{-1}$; said carbon catalyst (a) being prepared by pyrolyzing a resinous polymer, and (b) containing less than about 0.1 weight percent of each of the platinum group metals and the metals of Groups IB and IIB.

* * * * *